US005716406A

United States Patent [19]

Farber

[11] Patent Number: 5,716,406
[45] Date of Patent: Feb. 10, 1998

[54] METHOD OF REDUCING MEDICAL DEVICE RELATED INFECTIONS

[75] Inventor: Bruce Farber, Port Washington, N.Y.

[73] Assignee: North Shore University Hospital Research Corp., Manhasset, N.Y.

[21] Appl. No.: 279,585

[22] Filed: Jul. 25, 1994

Related U.S. Application Data

[60] Division of Ser. No. 35,553, Mar. 23, 1993, Pat. No. 5,366,505, which is a continuation-in-part of Ser. No. 802,891, Dec. 6, 1991, abandoned.

[51] Int. Cl.$^6$ ............................................. A61F 2/02
[52] U.S. Cl. ........................... 623/11; 427/2.1; 427/2.14; 427/2.24; 604/172; 424/405; 424/422; 424/423
[58] Field of Search ........................ 427/224, 2.14, 427/2.1; 623/11; 604/172; 424/422, 405, 423

[56] References Cited

U.S. PATENT DOCUMENTS

| | | | |
|---|---|---|---|
| 3,695,921 | 10/1972 | Shepherd et al. | 427/2.28 |
| 4,343,788 | 8/1982 | Mustacich et al. | 514/578 |
| 4,479,795 | 10/1984 | Mustacich et al. | 604/53 |
| 5,512,055 | 4/1996 | Domb et al. | 604/265 |

FOREIGN PATENT DOCUMENTS

| | | |
|---|---|---|
| WO 89/03232 | 4/1989 | WIPO. |
| WO 92/15286 | 9/1992 | WIPO. |

OTHER PUBLICATIONS

Goodman & Gilman's *"The Pharmacological Basis of Therapeutics"*, 9th ed., 1996, Chapter 27, pp. 617–657.
Goodman & Gilman's *"The Pharmacological Basis of Therapeutics"*, 9th ed., 1996, Chapter 66 pp. 1664–1669.
Susan Budavari, Ed., The Merck Index, 11th edition, 1989, pp. 163, 357, 495, 623, 625, 657, 776, 824, 836, 1322 and 1419.

Farber and Wolff, *The Use of Nonsteroidal Antiinflammatory Drugs* . . . . JID 1992:166, pp. 861–865.

Farber and Wolff, *The Use of Salicylic Acid To Prevent The Adherence* . . . , Journal of Urology, vol. 149, Mar. 1993, pp. 667–670.

Farber and Wolff, *Salicylic Acid Prevents The Adherence of Bacteria* . . . , Journal of Biomedical Material Research, vol. 27, 1993, pp. 599–602.

Farber, B. et al., "The Use of Nonsteroidal Antiinflammatory Drugs to Prevent Adherence of Staphylococcus epidermidis to Medical Polymers," *The Journal of Infectious Diseases*, vol. 166, No. 4, Oct. 1992, pp. 861–865.

Farber, B. et al., "Staphylococcus epidermidis Extracted Slime Inhibits the Antimicrobial Action of Glycopeptide Antibiotics," *The Journal of Infectious Diseases*, vol. 161, No. 1, Jan. 1990, pp. 37–40.

*Primary Examiner*—Vasu Jagannathan
*Assistant Examiner*—John J. Guarriello
*Attorney, Agent, or Firm*—Kenyon & Kenyon

[57] ABSTRACT

The growth of microorganisms on catheters and other medical devices is inhibited by slime-inhibiting compounds. Slime-inhibiting compounds include salicylic acid and other NSAID.

16 Claims, No Drawings

METHOD OF REDUCING MEDICAL DEVICE RELATED INFECTIONS

This application is a division of application Ser. No. 08/035,553 filed Mar. 23, 1993, now U.S. Pat. No. 5,366,505, which is a continuation-in-part of Ser. No. 07/802,891 filed on Dec. 6, 1991, now abandoned.

BACKGROUND OF THE INVENTION

The frequency of infection associated with the use of invasive medical devices such as insertable as well as implantable devices is well documented. In the case of insertable devices such as catheters, the rate of infection necessitates frequent replacement. In the case of implantable devices such as prosthetic devices, infections interfere with adaptation to the device. In either case, life-threatening septicemia can result from such infections.

The pathophysiology of medical device related infections is complex. Many factors influence the risk and type of infection. These include factors related to the host, to the medical device and to the virulence and inoculum of the infecting organism. Hundreds of medical publications have investigated and documented the variables that contribute to these factors. It has been well established that the overwhelming majority of medical device associated infections occur when bacteria colonize and then migrate along the medical device until they gain access to the bloodstream. Accordingly, the ability of bacteria to adhere to a medical device is important to the successful establishment of an infection.

The role of bacterial surface polysaccharides in adherence is well established. Over 12 years ago a series of experiments demonstrated the ubiquitous nature of these polysaccharides. Surface polysaccharides are found on most bacteria and fungi. When confronted with a specific lectin, the surface polysaccharides generate a glycocalyx that surrounds the bacteria and adhering surface. The glycocalyx consists of a mass of long polysaccharide fibers and appears to have several functions. It may act as a source of nutrition for the bacteria. It may serve as a physical barrier. Most importantly, surface polysaccharides determine the specific surface interactions of the bacterial cell.

This phenomena has far reaching effects. For example the ability of *Streptococcus mutans* to colonize teeth, *Streptococcus salivarius* to colonize gums, *Bacteroides fragilus* to colonize the intestine, and Group A streptococci to colonize the throat and skin are all manifestations of a complex interaction between specific surface polysaccharides and specific lectins, which are proteins that bind to specific polysaccharides.

The importance of bacterial surface and medical device related infections is best illustrated by coagulase negative staphylococci. *S. epidermidis*, the most important and common of the coagulase negative staphylococci, was previously considered a non-pathogenic organism. It has now emerged as the most common cause of foreign body infection and nosocomial sepsis. It is the major cause of prosthetic valve endocarditis, vascular graft infection, artificial hip and knee infection, and catheter related sepsis. Although less virulent than *S. aureus* and many other bacteria, it is highly resistant to most antimicrobials except vancomycin and rifampin.

In the early 1980's, electron microscopy studies demonstrated that certain strains of *S. epidermidis* produce an extracellular slime like substance. The extracellular slime is a complex substance composed mostly of polysaccharide.

The production of slime by an organism enables it to adhere to surfaces of insertable or implantable devices and cause infection. The slime appears to contain a galactose rich polysaccharide "adhesive" which mediates attachment of the organism to polymers. It also contains a polysaccharide substance that accumulates after adherence occurs and cements the organism to the medical device.

Besides adhesion, the slime appears to have other functions. It binds to glycopeptide antibiotics including vancomycin. This may explain why most *S. epidermidis* infections do not respond to antimicrobial therapy alone. When infection occurs on an inserted or implanted device, removal of the device is usually required. Slime also interferes with certain immune responses.

The extracellular slime of *S. epidermidis* is really a manifestation of exuberant production of surface polysaccharide. The quantitative production appears to be regulated by a complex mechanism that turns on and off production based upon the local environment. Although *S. epidermidis* has been the focus of much of the research on foreign-body infections, this concept has been studied in other organisms. Colonization by Pseudomonas species on the interior surface of PVC and other pipes has demonstrated a glycocalyx mass that shields organisms from disinfectants including chlorine, phenolics, quaternary-ammonium, and iodophor disinfectants. Once a bacterial glycocalyx is formed, it is very difficult to break down.

The development of polymers that contain antimicrobial properties has important implications for both medicine and industry. Aside from factors related to bacterial polysaccharides, the coating of the foreign body by proteins (albumin, fibronectin, platelets) from the host, as well as a variety of factors related to the polymer itself undoubtedly affect the risk of infection.

Several approaches have been utilized to produce medical devices made of or with polymers with antimicrobial properties, as described, for example, in U.S. Pat. Nos. 4,769,013, 4,713,402 and 4,886,505. Antimicrobial agents can be incorporated during the production process or grafted into the surface as described in U.S. Pat. No. 4,925,668. However, even broad-spectrum antibiotics eventually lead to the selection of resistant organisms. Selection of opportunistic fungi, resistant gram negative rods, *S. epidermidis*, and enterococci is likely. In addition, unless the "delivery" of the antibiotic is rapid, potent, and long lasting, formation of the protective glycocalyx will prevent its effectiveness. In addition, many antibiotics produce allergic reactions in some patients.

The present invention is based on an alternative approach, namely interference with the adherence of bacteria to polymeric surfaces of medical devices. Studies have demonstrated that both the degree of slime and adhesive production influence and correlate with the degree of bacterial adherence to silastic catheters. *S. haemolyticus*, unlike *S. epidermidis* do not produce slime and are a very uncommon cause of catheter related infection. As described herein, substances that prevent or reduce the production of slime by bacteria reduce their adherence and thus reduce the level of growth of microorganisms on the surface of the inserted or implanted devices.

It has been observed that sodium salicylates and certain other compounds can interfere with the production of capsule polysaccharide production in *Klebsiella pneumonia*. Salicylate binds to lipids in the outer membrane where biosynthetic enzymes are located. It has been postulated that capsular polysaccharide is the backbone of glycocalyx formation.

An object of the present invention is to use salicylates and other nonsteroidal anti-inflammatory drugs ("NSAID"), as well as other compounds such as chelating agents, to prevent the production of slime or surface polysaccharides in target microorganisms, thereby preventing their adherence and growth on materials used in medical devices.

A further object of the present invention is to utilize slime or surface-polysaccharide-inhibiting compounds which have, in addition, anti-platelet and thrombotic properties. This is particularly useful since the formation of the glycocalyx may be determined in part by platelets and fibronectin. The use of such compounds may decrease the incidence of thrombophlebitis as well as infection.

It is a further objective of the present invention to reduce bacterial growth on implanted devices using compounds that are relatively non-toxic.

These and other objectives are accomplished by the invention described in detail below.

SUMMARY OF THE INVENTION

As embodied herein, the foregoing and other objects are achieved by the present invention which involves the use of salicylic acid and other similarly-acting compounds to inhibit the formation of microbial slime or surface polysaccharides, thus interfering with their ability to adhere to invasive medical devices and thereby cause infection.

DETAILED DESCRIPTION OF THE INVENTION

Described herein is a method for preventing the adherence and growth of microorganisms on catheters as well as other insertable or implantable medical devices using slime-inhibiting compounds. Reduction of the slime production by such microorganisms reduces their ability to adhere to the medical device thus reducing the risk of infection and nosocomial sepsis.

The present invention is based on the discovery that by inhibiting the adherence of bacteria to catheters and other medically related foreign bodies, the risk of infection and sepsis can be reduced, and the residence time in which the medical device can remain in the body can be increased. The adherence of the bacteria to the medical device is inhibited by using a compound that interferes with the ability of the microorganism to produce a slime. The term slime, as used herein, includes the extracellular and capsular substance, composed to a large extent of extracellular polysaccharide, which is produced by many microorganisms, including coagulase negative staphylococci such as S. epidermidis and S. aureus, Escherichia coli, Pseudomonas and other gram negative rods, as well as other microorganisms.

A slime-inhibiting compound is a substance or collection of substances which inhibits either production of the slime produced by a microorganism, or a component of the slime, such as the polysaccharide component. Regardless of the component of the slime that it inhibits, the slime-inhibitor reduces the ability of a microorganism to adhere to a polymeric surface. Slime inhibiting compounds include, but are not limited to, NSAID such as acetylsalicylic acid (aspirin), salicylate, bis-salicylate, benzyl-benzoic acid, diflunisal, fendosal, indomethacin, acemetacin, cinmetacin, sulindac, tolmetin, zomepirac, diclofenac, fenclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, flunixin, clonixin, phenylbutazone, feprazone, apazone, trimethazone, mofebutazone, kebuzone, suxibuzone, piroxicam, isoxicam and tenoxicam, as well as chelating agents.

As contemplated herein, medically implanted or inserted devices include those inserted percutaneously or through an orifice, or implanted for short or long ranges of time as well as permanently. Such devices include catheters as well as sutures, heart valves, grafts such as vascular or other tissue grafts and prosthetic devices such as artificial hips and knees. Such devices are generally made of a polymeric material such as silastic or other silicone-based material, polyethylene tecephtalate (PET), dacron, knitted dacron, velour dacron, polyglacin, chromic gut, nylon, silk, bovine arterial graft, polyethylene (PE), polyurethane, polyvinyl chloride, silastic elastomer, silicone rubber, PMMA [poly-(methyl methacrylate), latex, polypropylene (pp), titanium, cellulose, poly vinyl] alcohol (PVA), poly (hydroxyethyl methacrylate (PHEMA), poly (glycolic acid), poly (acrylonitrile) (PAN), floroethylene-co-hexafluoropropylene (FEP), teflon (PTFE) and Co—Cr alloys.

The slime inhibitor may be added to the material on which microbial growth is to be inhibited by spraying, dipping, soaking, or by incorporation into the material itself. Alternatively, the inhibitor may be incorporated into a secondary polymer used to coat the surface of the medical device. Such a secondary polymer may have slow release properties that allow for the gradual release of the inhibitor into the microenvironment of the device.

Several of the slime-inhibitors used to practice the present invention have additional therapeutic properties. Accordingly, their use is often suggested in conjunction with medical implants, ostensibly to decrease swelling around the site of implantation. For example, in U.S. Pat. No. 4,769,013 the use of salicylate as an analgesic or anesthetic in conjunction with a medical material is suggested. In addition, drugs described herein have been incorporated into drug delivery devices because of their therapeutic properties. However, the level of compound used in such circumstances must be relatively high to achieve the desired therapeutic result.

In contrast, and because the present invention contemplates use of a level of compound sufficient only to inhibit slime formation within the microenvironment of the device, the levels of the compounds described herein are below the level necessary for therapeutic systemic effect. Generally, the amount of inhibitor utilized herein to prevent production of polysaccharide production and adherence to the device, as measured by concentration on the surface of the device, is between about 1 and about 20 mM. This level is believed to be sufficient to decrease the incidence of thrombophlebitis associated with the device due to the known anti-platelet activity of NSAID.

According to one preferred embodiment, distribution of the inhibitor on the device to be inserted or implanted is accomplished by incubating the device in a solution containing the slime-inhibitor. The inhibitor is suspended in a solution, most preferably an alcohol-based solution, at a concentration of between about 1 mM and 1M. The device is incubated within such a solution for between about 15 minutes and 24 hours at a temperature of between about $-20°$ C. to $25°$ C. after which it is air dried.

Preferably the coating is performed at between about $-20°$ C. and $10°$ C. In general, use of the inhibitor in conjunction with alcohol has been found to increase the polysaccharide inhibiting properties. When the surface to be treated is teflon, however, the alcohol decreases the effectiveness of the slime-inhibitor. When alcohol is used, optimum results are often obtained by incubating at $-20°$ C.

Another method makes use of tridodecylemthylammonium chloride (TDMAC) or benzalkonium chloride to bind the slime-inhibiting substance to the catheter or medical device. TDMAC has previously been used to coat catheters and other medical devices with antibiotics and heparin.

The ability of a compound to inhibit the production of slime by a microorganism and thereby inhibit its growth on a medically insertable or implantable device can be measured by several methods. Once the device is coated or impregnated with the compound, the device is exposed to a source of bacteria over a specified period of time, after which the device is washed and the growth of the bacteria on the device measured. Such measurements may include colony counts or other means of quantifying microorganisms, such as chemiluminescent or bioluminescent assay, which monitor a particular metabolite as a means of quantifying bacterial load or by radiolabelling techniques.

A suitable methodology for analyzing the effectiveness of an inhibitor in preventing microbial growth on catheters or other medically insertable or implantable devices is described in Example 21.

Although the current application deals with medical devices, this concept can be applied in a number of industrial areas. Glycocalyx formation by gram negative rods occurs in PVC and other plumbing supplies. The formation of this glycocalyx has been shown to contaminate the manufacturing process of products in which sterility is vital. Coating such pipes with a NSAID may minimize this problem.

In addition, similar applications can be considered in the marine industry where water-borne organisms cause destruction. Also contemplated by the present invention is the use of the NSAID as additives to waterproofing and coatings for boats and other marine supplies.

EXAMPLES

Example 1

The effect of sodium salicylate on the growth characteristics of various organisms was studied. A slime producing strain of coagulase negative staphylococcus was grown in increasing concentrations of salicylate in two different types of media, chemically defined media (CDM) and tripticase soy broth (TSB). The resultant bacterial counts were as follows:

|         | CDM | TSB |
|---------|-----|-----|
| Control | $2.3 \times 10^9$ | $1.2 \times 10^9$ |
| 1 mM    | $7.2 \times 10^8$ | $1.4 \times 10^9$ |
| 5 mM    | $8.3 \times 10^8$ | $5.7 \times 10^8$ |
| 10 mM   | $5.7 \times 10^8$ | $5.2 \times 10^8$ |
| 25 mM   | $2.3 \times 10^8$ | $3.2 \times 10^7$ |

These studies demonstrated that salicylate does not have antimicrobial properties. It did not inhibit the growth of coagulase negative staphylococci in either chemically defined media or in commercially prepared tryticase soy broth. Similar growth curves were obtained with gram negative rods including *E. coli* and Pseudomonas.

Example 2

As a crude measure of its ability to influence the production of slime, the yield of slime by weight from a one liter broth culture *S. epidermidis* grown in the presence of increasing concentrations of salicylate was used to measure the ability of salicylate to influence the production of slime.

| Concentration | Yield |
|---------------|-------|
| Control | 86 mg. |
| 1 mM    | 68 mg. |
| 5 mM    | 58 mg. |
| 25 mM   | 47 mg. |

As noted, the amount of slime decreased with increasing concentrations of salicylate.

Example 3

The effect of increasing concentrations of salicylate on the production of slime by *S. epidermidis* was measured by using a spectrophotometric assay. The results were as follows:

| Concentration (mM) | Optical Density |
|--------------------|-----------------|
| Control | 1.5 |
| 1 mM    | 1.4 |
| 2 mM    | 1.3 |
| 5 mM    | .5  |
| 10 mM   | .08 |
| 25 mM   | .01 |

A progressive fall in the optical density with increasing concentrations of salicylate, most evident at 5 mM and above, was observed.

Example 4

Selected strains of slime-producing coagulase negative staphylococci (*S. epidermidis*) were grown in various concentrations of salicylate. After 24 hours growth, various types of catheters were placed in high concentrations of the organisms for 15 minutes. This assay exposed the catheters to a high concentration of organisms for a short period of time. The catheters were washed three times, and rolled onto agar in a standardized manner. The agar plates were incubated overnight, and the number of colonies counted. The percent inhibition of adherence was calculated with the following formula:

$$\% \text{ inhibition} = 100 - \frac{(\# \text{ of } CFU \text{ adhering in salicylate})}{(\# \text{ of } CFU \text{ adhering in control})} \times 100$$

with the following results:

|              | Concentration | Adherence (CFU plate) | Inhibition |
|--------------|---------------|------------------------|------------|
| Polyurethane |   |     |     |
|              | 0 | 229 |     |
|              | 1 Mm | 236 | N.I. |
|              | 2 Mm | 48  | 79% |
| Teflon       |   |     |     |
|              | 0 | 171 |     |
|              | 1 mM | 50 | 71% |
|              | 5 mM | 22 | 87% |

| | Concentration | Adherence (CFU plate) | Inhibition |
|---|---|---|---|
| Silastic | | | |
| | 0 | 325 | |
| | 1 mM | 265 | 19% |
| | 2 mM | 149 | 54% |
| | 25 mM | 77 | 76% |
| PVC | | | |
| | 0 | 378 | |
| | 1 mM | 157 | 58% |
| | 5 Mm | 85 | 85% |

Example 5

A similar assay to that used in Example 4 was performed using S. aureus and E. coli. This was done using a silastic catheter. The results were as follows:

| | Adherence (CFU/plate) | | Adherence (CFU/plate) | |
|---|---|---|---|---|
| Concentration | E. coli | % Inhib. | S. aureus | % Inhib. |
| 0 | 90 | | 285 | |
| 1 mM | 32 | 64 | 154 | 46% |
| 5 mM | .5 | 99 | 112 | 61% |

This demonstrated an effect with E. coli and S. aureus that was similar to that observed with S. epidermidis.

Example 6

Catheter segments were incubated overnight in salicylate and compared to control catheters that were not incubated in salicylate to determine whether the salicylate would coat the polymer surface.

Catheter segments were incubated in 100 mM salicylate overnight at 37° C., pH 7.0. The catheters were then dried, and dipped into a 5×10$^5$ CFU/ml coagulase negative staphylococci for 15 minutes. All studies were done in triplicate.

| | Adherence (CFU/plate) | | |
|---|---|---|---|
| | Control | Salicylate | Inhib. |
| Silastic | 600 | 317 | 47% |
| Polyurethane | 33 | 20 | 27% |
| Teflon | 35 | 13 | 63% |
| | 17 | 3 | 82% |
| PVC | 85 | 50 | 41% |

Example 7

Teflon, PVC, and silastic catheters were incubated in 100 mM salicylate at 37° overnight and were incubated with high concentrations of bacteria (10$^7$–10$^8$ CFU/ml). After incubation, the catheters were washed three times, then rolled onto agar and incubated. The colonies were counted. The results were as follows:

| | Teflon | PVC | Silastic |
|---|---|---|---|
| E. coli | | | |
| Control | 8.0 | 13 | 211 |
| Salicylate | 13.0 | 9 | 103 |
| Inhibition | 0% | 29% | 51% |
| P. aeruginosa | | | |
| Control | 80 | 275 | 59 |
| Salicylate | 1 | 200 | 3 |
| Inhibition | 100% | 27% | 94% |

The inhibition was most obvious with Pseudomonas regardless of the type of polymer used. The E. coli did not adhere as well as pseudomonas regardless of the catheter type.

Example 8

A study similar to that described in Example 7 was done with a smaller inoculum of (10$^5$ CFU/ml) of S. aureus with the results as follows:

| | Adherence CFU/plate) | Inhibition |
|---|---|---|
| Teflon | | |
| Control | 147 | |
| Salicylate | 54 | 63% |
| PVC | | |
| Control | 192 | |
| SAL | 136 | 30% |
| Silastic | | |
| Control | 296 | |
| SAL | 224 | 24% |

Example 9

Silastic and polyurethane catheters were incubated in 95% EtOH and 95% EtOH and 200 mM salicylate at pH 7.0 for 2 hours at –20° C. The catheters were air dried and incubated in broth containing 10$^5$ CFU/ml S. epidermidis for 15 minutes at 37° C. The catheters were then washed and rolled onto agar. The results on two identical experiments were as follows:

| | Control | Salicylate | Inhibition |
|---|---|---|---|
| Trial 1 | | | |
| Polyurethane | 143 | 91 | 36% |
| Silastic | 461 | 35 | 92% |
| Trial 2 | | | |
| Silastic | 37 | .67 | 98% |
| PVC | 60 | 50 | 17% |
| Teflon | 19 | 20 | 0% |
| Polyurethane | 138 | 57 | 59% |

Example 10

Similar experiments to those described in Example 9 were conducted using E. coli. A high concentration of organisms (10$^6$) was used. Catheter segments were incubated for 2 hours in 200 mM salicylate in 95% ethanol. The catheters were dried and placed in the E. coli cultures at room temperature. They were allowed to incubate for 18 hours. The results were as follows:

|  | (CFU/plate) | | |
| --- | --- | --- | --- |
| Catheter | Control | Salicylate | Inhibition |
| Polyurethane | 77 | 10 | 88% |
| PVC | 21 | 3 | 86% |
| Silastic | 50 | 3 | 96% |

Example 11

Silastic catheters prepared as described in Example 9 were incubated in cultures of *S. epidermidis* for three days at 37° C.

| CFU/plate Control | Salicylate | Inhibition |
| --- | --- | --- |
| 15 | 6 | 60% |

Example 12

Silastic catheters prepared as described in Example 9 were incubated in cultures of *E. coli* for three days. ($10^5$ CFU/ml).

| CFU/plate Control | Salicylate | Inhibition |
| --- | --- | --- |
| 1400 | 700 | 50% |

Example 13

Polyurethane and silastic catheters were soaked overnight in varying concentrations of salicylic acid in ethanol at –20° C. and then exposed to coagulase negative staphylococci and *E. coli* for 4 hours at 37° C. They were washed and rolled as per the protocol described in Example 9.

|  | pH | Count/Plate | CFU/mm |
| --- | --- | --- | --- |
| Coagulase Negative Staphylococci (Polyurethane - tubing) | | | |
| Control | 7.33 | >400 | 20.0 |
| Salicylate 200 mM | 7.19 | 310 | 14.6 |
| Salicylate 600 mM | 6.77 | 50 | 2.4 |
| Ibuprofen 400 mM | 7.22 | 233 | 11.5 |
| Ibuprofen 200 mM | 7.02 | 352 | 18.1 |
| *E. coli* (silastic tubing) | | | |
| Control |  | 250 | 12.0 |
| Salicylate 200 mM |  | 226 | 11.6 |
| Salicylate 600 mM |  | 32 | 1.6 |
| Ibuprofen 400 mM |  | 238 | 12.0 |
| Ibuprofen 200 mM |  | 185 | 9.6 |

Example 14

Catheters treated with salicylate and ibuprofen as described in Example 9 were incubated in phosphate buffered saline having a concentration of $10^3$ CFU/ml *E. coli* for six days at 37° C. This produced a constant concentration of organisms.

| Coating | (CFU/plate) | Inhibition |
| --- | --- | --- |
| Control | 240 |  |
| 200 mM salicylate | 121 | 50% |
| 100 mM Ibuprofen | 70 | 71% |

Despite six days of incubation, the inhibition was impressive. It was greater with ibuprofen than salicylate in this experiment.

Example 15

Polyurethane and silastic catheters were incubated in ibuprofen, acetyl-salicylate, and benzoyl-benzoic acid with 95% ethanol for 2 hours. The catheters were then incubated in *S. epidermidis* as described in Example 9. The results were as follows:

|  | (CFU/plate) | Inhibition |
| --- | --- | --- |
| Polyurethane | | |
| Control | 295 |  |
| Acetyl-Salicylate (200 mM) | 127 | 57% |
| Salicylate (200 mM) | 270 | 9% |
| Ibuprofen (100 mM) | 166 | 44% |
| Benzyl benzoic (100 mM) | 333 | 0% |
| Silastic | | |
| Control | 52 |  |
| Acetyl-Salicylate (200 mM) | 7 | 86% |
| Salicylate (200 mM) | 33 | 36% |
| Benzyl benzoic (100 mM) | 9 | 83% |

Example 16

Polyurethane catheters were preheated overnight at 67° C. and coated in the compounds listed below at –20° C. in 95% ethanol. They were then incubated in coagulase negative staphylococci at 37° for 18 hours, and washed three times in phosphate buffered saline. ATP was extracted with extralight and read with firelight in a dynatech luminometer reader.

|  | Units of light (measured at 48°) |
| --- | --- |
| Control | .62 |
| Salicylate | .19 |
| Acetylsalicylate | .06 |
| Acetaminophen | 2.4 |
| Ibuprofen | .32 |
| Phenylbutazone | .02 |
| Indomethacin | .07 |

The units of light are a reflection of the amount of ATP released and bacteria that have adhered to the polymer. The experiment was repeated, but by growing the organisms directly in the microlite wells. Cultures of coagulase negative staphylococci were grown in the presence of 2 mM NSAID in microlite wells, washed and treated with extralight and firelight.

|  | Units of light (measured at 48°) |
| --- | --- |
| Control | 89.0 |
| Acetylsalicylate | 13.0 |
| Salicylate | 15.0 |

| | Units of light (measured at 48°) |
|---|---|
| Ibuprofen | 9.0 |
| Acetaminophen | 108.0 |
| Indomethacin | 9.2 |
| Phenylbutazone | 19.1 |

Example 17

Several experiments were done with gram negative rods in urine instead of broth. Silastic catheters were prepared as previously described and were incubated for 4–5 hours at 37° C. All studies were done in triplet.

| Silastic Catheter | CFU/mM | Inhibition |
|---|---|---|
| *E. coli* Incubated in Urine (5 Hours) | | |
| Control | 25.0 | |
| Salicylic Acid (200 mM) | 17.0 | 31% |
| Salicylic Acid (600 mM) | 1.5 | 94% |
| *Klebsiella pneumoniae* (4 Hours) | | |
| Control | 14.0 | |
| Salicylic Acid (200 mM) | 4.9 | 65% |
| Salicylic Acid (600 mM) | 1.8 | 87% |
| *E. Aerogenes* in Urine (5 Hours) | | |
| Control | 15.5 | |
| Salicylic Acid (200 mM) | 9.8 | 37% |
| Salicylic Acid (600 mM) | 4.3 | 73% |

Example 18

In an attempt to determine the length of the observed effect, silastic catheters were incubated in salicylic acid as described, and then placed in sterile urine for 4 days. At the end of this period, the catheters were removed and then placed in a broth culture of *E. coli*. Results are the mean of three trials.

| Silastic Catheter | CFU/mM | Inhibition |
|---|---|---|
| Control | 13.2 | |
| Salicylic Acid (200 mM) | 9.6 | 27% |
| Salicylic Acid (600 mM) | 2.9 | 78% |

This experiment demonstrated that the coating is not lost immediately after the catheter is placed in an aqueous solution.

Example 19

*S. epidermidis* was radiolabeled by including 1 µCi of ($^{14}$C-sodium acetate) in the preliminary overnight culture. The catheter segments were exposed to the broth culture overnight at 37° C. The catheters were vigorously washed in saline, air dried, and placed in scintillation vials for counting.

| | TSB with NaAc (1.2 - $^{14}$C) Overnight at 37° C. | |
|---|---|---|
| Silastic Catheter | | CPM |
| Control | | 1481.0 |
| Salicylic Acid (200 mM) | | 528.0 |
| Salicylic Acid (600 mM) | | 165.0 |

Example 20

Another embodiment uses tridodecylemthylammonium chloride (TDMAC) or benzalkonium chloride which coats the catheters and also binds to the salicylates. Silastic catheters that had been preheated were coated in 5% TDMAC in ethanol for 40 minutes at room temperature. The catheter segments were vigorously washed with sterile water and air dried. The segments were then immersed in ethanol, 200 mM salicylic acid and 600 mM salicylic acid overnight at −20° C. The catheters were air dried and immersed in a trypticase soy broth culture of *E. coli* or *S. epidermidis* at 37° C. Catheters were washed 3 times in 3 changes of sterile saline and rolled on Mueller-Hinton Agar plates. The plates were incubated overnight at 37° C. and the colonies were counted.

| | | CFU/Plate | CFU/mM | Inhibition |
|---|---|---|---|---|
| *E. coli* | Control | 143.0 | 6.5 | |
| (5 Hour | Salicylic Acid (200 mM) | 23.0 | 1.1 | 83% |
| Incubation) | Salicylic Acid (600 mM) | 1.5 | 0.07 | 99% |
| *S. epidermidis* | Control | 91.0 | 4.3 | |
| (Overnight | Salicylic Acid (200 mM) | 81.0 | 3.9 | 9% |
| Incubation) | Salicylic Acid (600 mM) | 52.0 | 2.6 | 40% |

Example 21

The following is a recommended method for determining whether a particular compound inhibits slime production and adherence to a medical device:

1. Prepare test coating solutions at desired concentrations. Prepare sterile 3 cm section of tubing.
2. Incubate tubing pieces in sterile water at 67° C. overnight, dry 1 hour, then expose to test solutions and controls at −20° C. for 2 hours. Ensure that all tubing are immersed in solution.
3. Remove the tubing and dry coated samples in a sterile field. Mark tubing 1 cm from end.
4. Assemble a sterile 3 cm syringe with a sterile industrial blunt syringe which will fit securely into the tubing to be tested.
5. Attach the marked end of the 3 cm lengths of coated tubing to the needle. Withdraw the plunger from the syringe to about the 2 or 3 cc mark.
6. Place 15 ml of a $10^6$ bacterial suspension into a sterile 50 cc tube and place up to 3 tubes into each tube. Incubate at 37° C. for 15 minutes. The length of incubation and inoculum size can be varied.
7. Transfer each tubing segment into a separate 15 ml sterile tube containing approximately 5 ml of sterile saline. Each tube is vigorously washed by drawing saline back and forth through the tube 3 times.
8. The process is repeated until a total of 3 washes in 3 separate saline tubes is completed.
9. A 1 cm segment of the distal catheter is cut off and discarded.

10. The remaining 2 cm section was quantitatively rolled over a blood agar plate in 4 directions. The plates are incubated overnight a 37° C. and the colonies are counted.

11. The catheter segments are carefully measured so that the number of CFU/mm catheter can be calculated.

I claim:

1. A method of inhibiting growth of microorganisms on a medical device inserted or implanted in a mammal comprising:

exposing said medical device, prior to insertion or implantation, in a solution, said solution having a concentration of between about 1 mM and about 1M of an NSAID to impart to the device a concentration of said NSAID that inhibits or prevents growth of microbial biofilm in the microenvironment of a surface of said device, but which concentration is otherwise insufficient to cause a substantial therapeutic systemic effect in a mammal in which said device is inserted or implanted;

removing said medical device from said solution;

drying said medical device; and inserting or implanting said medical device in the mammal.

2. A method of inhibiting growth of microorganisms on a medical device inserted or implanted in a mammal comprising:

coating said medical device, prior to insertion or implantation, with a polymer, said polymer having a concentration of between about 1 milliMolar and about 1 Molar of an NSAID to impart to the device a concentration of said NSAID that inhibits or prevents growth of microbial biofilm in the microenvironment of a surface of said device, but which concentration is otherwise insufficient to cause a substantial therapeutic systemic effect in a mammal in which said device is inserted or implanted; and implanting or inserting said medical device in the mammal.

3. A method of inhibiting growth of microorganisms on a medical device implanted or inserted in a mammal comprising:

distributing on said medical device prior to insertion or implantation an effective amount of an NSAID, said effective amount being sufficient to inhibit or prevent production of microbial biofilm in a microenvironment of a surface of said device, but which amount is insufficient to cause a substantial therapeutic effect in a mammal into which the device is inserted or implanted; and implanting or inserting said medical device in the mammal.

4. The method according to claim 3 wherein the effective amount of NSAID distributed on the surface of said medical device is in the range of from about 1 mM to about 20 mM.

5. A method according to any one of claims 1, 2 or 3 wherein said NSAID is selected from the group consisting of salicylic acid, sodium salicylate, acetylsalicylic acid, bissalicylate, benzyl-benzoic acid, diflunisal, fendosal, indomethacin, acemetacin, cinmetacin, sulindac, tolmetin, zomepirac, diclofenac, fenclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, funixin, clonixin, phenylbutazone, feprazone, apazone, trimethazone, mofebutazone, kebuzone, suxibuzone, piroxicam, isoxicam and tenoxicam.

6. The method according to claim 5 wherein said NSAID is salicylic acid or sodium salicylate.

7. The method according to claim 5 wherein the NSAID is ibuprofen.

8. The method according to claim 3 wherein the NSAID is distributed on said medical device by incorporating the NSAID into materials used to make said medical device.

9. The method according to claim 8 wherein the materials used to make the medical device comprise a material selected from the group consisting of silastic or silicone-based material, polyethylene tecephtalate, polyglacin, polydioxanone, chromic gut, nylon, silk, dacron, knitted dacron, velour dacron, bovine arterial graft, polyethylene, polyvinyl chloride, silastic elastomer, silicon rubber, poly-(methyl methacrylate), latex, polypropylene, titanium, cellulose, polyvinyl alcohol, poly-(hydroxyethyl methacrylate), poly-(glycolic acid), poly (acrylonitrile), floroethylene-co- hexafluoropropylene, teflon, Co—Cr alloys, polyurethane, polyester, polytetrafluoroethylene and biological polymers.

10. The method according to claim 3 wherein the NSAID is distributed on the medical device by soaking the medical device in a solution containing the NSAID.

11. The method according to claim 10 or claim 1 wherein the medical device is soaked in said solution for a period of time in the range of from about ten minutes to about twenty four hours.

12. The method according to claim 10 wherein said solution comprises alcohol.

13. The method according to claim 12 wherein the alcohol is ethanol.

14. The method according to claim 10 wherein the medical device is soaked in said solution at a temperature of from about −20° C. to about 25° C.

15. The method according to claim 3 wherein the NSAID is distributed on the medical device by coating the device with a polymer containing said NSAID.

16. The method according to claim 15 or claim 2 wherein the polymer has slow release properties.

* * * * *